United States Patent [19]

Bahr

[11] 4,138,209
[45] Feb. 6, 1979

[54] APPARATUS FOR AUTOMATICALLY MELTING AND CASTING FUSIBLE MATERIAL

[75] Inventor: Werner Bahr, Duisburg, Fed. Rep. of Germany

[73] Assignee: Firma Richard Schoeps KG & Co. GmbH, Duisburg, Fed. Rep. of Germany

[21] Appl. No.: 871,485

[22] Filed: Jan. 23, 1978

[30] Foreign Application Priority Data

Jan. 25, 1977 [DE] Fed. Rep. of Germany ....... 2702818

[51] Int. Cl.² ...................... B22D 37/00; B22D 41/06
[52] U.S. Cl. .................................... 425/160; 164/157; 164/335; 222/593; 222/604; 266/240; 425/155
[58] Field of Search ............... 164/157, 266, 335, 338, 164/258; 222/593, 604, 605; 266/236, 240, 242; 425/155, 160, 317

[56] References Cited

U.S. PATENT DOCUMENTS

| | | | |
|---|---|---|---|
| 2,713,183 | 7/1955 | Winkler | 164/258 |
| 3,310,298 | 3/1967 | Huwyler et al. | 266/240 |

FOREIGN PATENT DOCUMENTS

422528  9/1974  U.S.S.R. .................................. 164/258

*Primary Examiner*—Robert D. Baldwin
*Attorney, Agent, or Firm*—Karl F. Ross

[57] ABSTRACT

An apparatus for casting a fusible material has a support on which is provided a row of melting burners and a parallel row of warming burners. A crucible holder on the support has a pair of bars forming a plurality of seats each above a respective one of the melting burners and each for a respective crucible. A slide having a plurality of mold holders is displaceable into a position with the mold holders above the warming burners. Once the material in the crucible holders has been melted by the melting burners the entire crucible-holding assembly may be agitated horizontally to homogenize this material. Thereafter the entire crucible-holding assembly is tipped up to pour the contents of the crucibles into the molds which have been preheated by the warming burners. The warming burners are then shut off and jets of compressed ambient-temperature gas are directed at the molds to cool the material therein and solidify same into a tablet or slug suitable for X-ray analysis.

20 Claims, 5 Drawing Figures

FIG. 3

APPARATUS FOR AUTOMATICALLY MELTING AND CASTING FUSIBLE MATERIAL

FIELD OF THE INVENTION

The present invention relates to an apparatus for melting and casting a fusible material. More particularly this invention concerns an apparatus for forming tablets of a material to be fused for subsequent X-ray study.

BACKGROUND OF THE INVENTION

In order to test various oxidizable materials such as ore, ash, slags, or heat-resistant materials of a similar nature it is necessary to melt these materials and cast tablets or slugs of them. Then the tablets or slugs can easily be analyzed by X-ray or fluoroscope techniques.

Thus it is normally necessary to melt in a small crucible, normally of platinum, a predetermined quantity of the material to be tested. Hence the material is melted and the entire melted mass inside the crucible is agitated to make it homogenous. Meanwhile a mold for casting a tablet or slug is preheated to a predetermined temperature. The homogenized molten material is then poured into the preheated mold which is then slowly cooled, whereupon a tablet or slug of predetermined size can be turned out of the mold.

Obviously the nine steps involved — filling the crucible with premeasured quantities, pouring the measured dose into the crucible, heating the crucible to melt the material, agitating the crucible to homogenize the material, prewarming a mold, pouring the homogenized and melted material into the mold, cooling the mold, turning the slug or tablet out of the mold, and cleaning the mold and crucible for reuse — take considerable time and represent an onerous succession of tasks.

Thus a machine is known having a carrousel with a plurality of angularly spaced holders for the crucibles. A crucible in one of the holders can be displaced angularly past one or more bunsen burners and a gas jet suitable for cooling the crucible. The operator must therefore charge into each crucible a quantity of the material to be tested along with the typical salt additive necessary for proper analysis later, then move the thus-filled crucible into position over the first burner. Once it is melted the material is agitated by hand over the second burner and thereafter emptied into a platinum mold that has been preheated, but can be afterward displaced over the air-cooling nozzle. This arrangement somewhat simplifies the operation, but nonetheless requires that virtually every stage be done by hand.

With such a semiautomatic arrangement it is possible to process a normal batch in approximately 32 minutes overall. Eight minutes are needed over the two burners to properly heat and homogenize the material, then the material must rest at least four minutes as it cools and hardens. Since two burners are provided it is therefore possible to complete a tablet every four minutes, using normally two operators to man the apparatus and make the slugs. If only six slugs are needed it therefore takes two men 32 minutes to form them. When a larger quantity is needed the amount of man-hours consumed is considerable, especially since two people must be employed, one operating the apparatus and another cleaning and refilling the crucibles.

OBJECTS OF THE INVENTION

It is therefore an object of the present invention to provide an improved apparatus for melting and then casting a fusible material.

Another object is the provision of such an apparatus which carries out most of the above-described nine tasks automatically.

Yet another object is to provide such an apparatus which can automatically be set to do most of the important operational steps in the fusing and forming of tablets of fusible material.

SUMMARY OF THE INVENTION

These objects are attained according to the present invention in an apparatus of the above-described general type having a melting burner and a warming burner. A crucible having at least one holding formation can be supported on a seat of a crucible holder. This seat is displaceable between a holding position in which the crucible is firmly held and a freeing position in which the crucible can easily be separated from the crucible holder. A mold holder is similarly provided on the support of the apparatus above the warming burner and a mold engageable in this mold holder can be positioned above the warming burner for preheating. Gripping means is provided for pivoting the entire support between a melting position with the crucible upright above the melting burner and a pouring position with the crucible tipped and over the warming burner. Control means connected to the crucible holder and to the tipping means maintains the crucible holder in the holding position at least when the crucible holder is in the pouring position, whereby on displacement of the crucible holder from the melting into the pouring position the fused material in the crucible can be poured into the mold without falling over of the crucible.

According to further features of this invention means is provided for agitating the crucible and crucible holder when in the melting position, and further means is provided for cooling the mold once the material has been poured into it. Thus of the nine steps of the operation five — melting, homogenizing, preheating the mold, pouring the material into the mold, and cooling the mold — are all carried out automatically.

According to another feature of this invention a row of such warming burners is provided adjacent a row of such melting burners and the crucible holder has a plurality of such seats each for a respective crucible. Similarly a plurality of mold holders and molds are provided so that it is possible to carry out a plurality of such sequences of operation all at the same time.

According to yet another feature of this invention the crucible holder includes a pair of bars flanking the warming burner and formed with respective recesses opening radially of the longitudinal axes of the respective bars. These bars can be displaced angularly between a position with their recesses directed generally upwardly and a position directed generally toward each other. The crucible has formations in the form of oppositely extending pins receivable in these recesses. When the recesses are directed toward each other the pins are locked tightly in place by the two bars, whereas when pivoted so that they both are directed generally upwardly the pins can be rested in the recesses but lifted therefrom.

In an operation where the turnaround time for the crucibles and molds is no more than four minutes it is possible to produce, using a residence time in the machine of eight minutes, a batch every 12 minutes. Furthermore the person who is cleaning the molds and crucibles and refilling the crucibles need be the only operator since once the machine is loaded it functions completely automatically. This therefore not only reduces the number of man hours at an absolute level, but reduces the personnel necessary in half, so that considerable savings are made with the apparatus according to the instant invention.

The agitating means is constituted by an electric motor connected via a belt or other flexible endless element to a pulley which is eccentrically journaled on a portion of the machine connected directly to the crucible holder but displaceable relative to the rest of the machine. When this eccentric rotation axis is vertical the effect of the rotation of the pulley will therefore be to agitate the crucible holder horizontally, thereby attaining good mixing without the possibility of spillage.

The mold holders may be ceramic or other heat-resistant arms carried on a slide so that the mold holders can be displaced from a position away from the burners of the machine into a position directly over the warming burners thereof. Automatic means may be provided for such displacement, in which case the mold holders may be displaceable from a position over the warming burner to a position over a cooling air nozzle, or the air nozzle may be movable into a position between a warming burner and the mold holder, in which latter case the warming burners are shut off during the cooling operation.

A control system incorporating timers for presetting the melting time, agitating time, and cooling time is provided which allows the machine to be set up for various different materials, as it is well known that some materials melt and/or cool more rapidly than others and that some need more or less agitation than others for proper homogenization. In any case once the machine is set for a given type of material the operation takes place automatically, and even if it is necessary to set the machine for each batch such a setting takes only a fraction of the amount of time that would be necessary to process the batch manually.

SPECIFIC DESCRIPTION

As shown in FIGS. 1-4 the apparatus according to this invention has a support frame 1 on which is provided a row of six relatively large primary or melting burners 2 and next to each one of the burners 2 a respective relatively small or secondary warming burner 3. Surrounding the parallel rows of burners 2 and 3 is a shaker frame 4 of U-shape in plan and having at each end of each of its legs a foot 5 of low-friction synthetic-resin material slidable on a horizontal support plate 6 carried at the upper end of a respective post 7. Thus the entire frame 4 can move limitedly horizontally relative to the burners 2 and 3 and the housing 1.

In addition, the U-shaped frame 4 carries at its rear end a horizontal plate 8 in which a pair of pulleys 9 are journaled about respective offset axes 10 to either side of the center of the unit. These pulleys 9 are connected together by a belt 80 and one of the pulleys is connected via a belt 81 to a motor 11. Thus as the motor 11 rotates the eccentrically journaled pulleys 9 the entire frame will move on its nylon feet 5 relative to the support 1.

A pair of square-section parallel holding rods 12 and 13 flank the row of burners 2. The rod 12 is journaled at its ends at 17 in the legs of the U-shaped agitating frame 4. In addition these rods 12 and 13 are both journaled at their ends in a pair of plates 14 and 15 fixed rigidly together by a tierod 16. A lever linkage 18 constituted by a lever arm 24 on the rear arm 12, a lever arm 19 on the front arm 13, and a diagonal link 25 connecting them can be operated by the piston rod 20 of a double-acting pneumatic cylinder 21 carried on the plate 14. Flexible feed lines 22 and 23 can be alternately vented and connected to a source of compressed air as will be described below.

Figure 2:
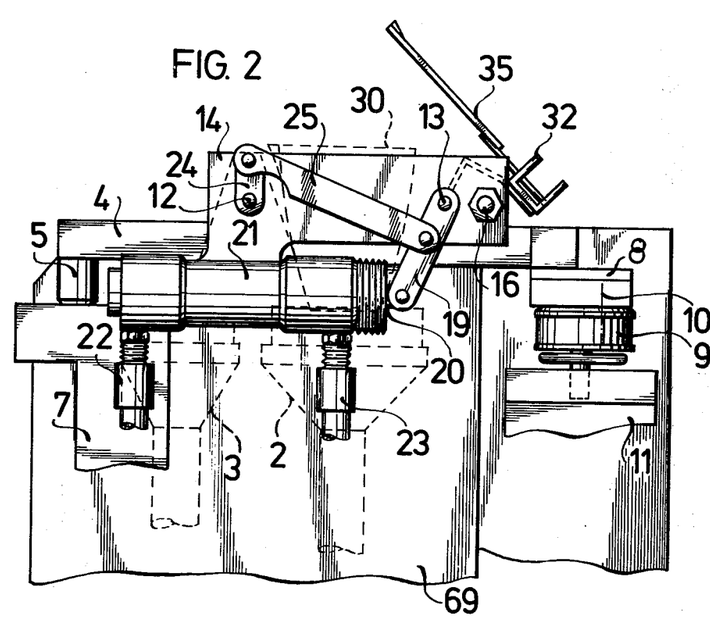
FIGS. 2, 3 and 4 are sections taken respectively along lines II — II, III — III, and IV — IV of FIG. 1.

Extension of the cylinder 21 from the position shown in FIG. 2 will pivot the two rods 12 and 13 oppositely about their respective parallel axes through approximately 45°. At the same time a holding bar 32 connected via brackets 34 to the rod 13 will be displaced arcuately through an angle of approximately 45°.

Figure 3:
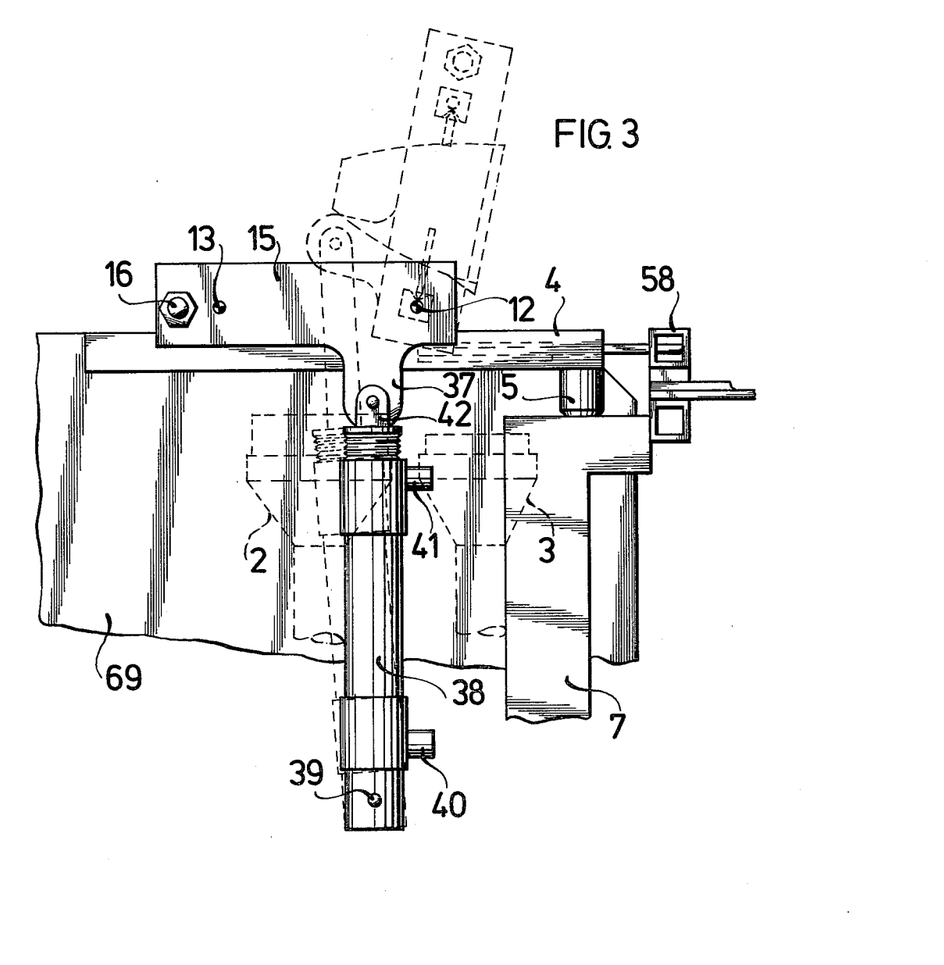

As best shown in FIG. 3 the rods 12 and 13 are formed with respective conical or outwardly flared recesses 27 and 26 centered on respective axes perpendicular to a respective flat face of the square-section rods 12 and 13. One such recess 26 is provided directly behind each burner 2 and two such recesses 27 directly in front of each burner 2. Platinum crucibles or sample holders 30 are each provided with a pair of forwardly extending legs or holding formations 29 engageable in the recesses 27 and a single rearwardly extending pin or holding formation 28 engageable in the respective recess 26. Thus it is possible to position a crucible 30 directly above each of the main burners 2 in a position with its pouring spout 31 directed forwardly toward the respective burner 3.

A crucible cover or lid 35 which leaves only the spout 31 uncovered is provided with a pair of rearwardly extending holding formations or legs 36 engageable in holes 33 in a U-section bar or channel 32 connected via the brackets 34 to the rod 13.

Thus displacement of the piston rod 20 backwardly or to the right as shown in FIG. 2 will have two main results. First of all it will pivot the two rods 12 and 13 through approximately 45°, thereby directly aligning the recesses 26 and 27 with each other. When thus aligned the holding pins 28 and 29 of the crucible 30 engaged in each of these set of three recesses 26 and 27 will be firmly locked in place. Such displacement will also swing the holding rod 32 forwardly and place the lid 35 of each crucible 30 firmly in place.

As shown in FIG. 3 the plate 15 has a downwardly extending tab or projection 37 to which is secured the piston rod 42 of a double-acting pneumatic cylinder 38 pivoted at its opposite end 39 on the downward extension of the frame 4. This cylinder 38 has flexible feed lines 40 and 41 which can alternately be pressurized and depressurized for operation of the cylinder 38 in either direction.

Thus extension upwardly of the cylinder 38 as shown in dot-dash lines in FIG. 3 will serve to pivot the entire tipping assembly constituted by the two rods 12 and 13, the endplates 14 and 15, the tierods 16 and the holding rod 32 with its brackets 34. If the rods 12 and 13 have been pivoted into the position with the recesses 26 and 27 directly facing each other the crucible held therein will be tipped up through at least 90° so that its contents can be poured out.

The burners 2 and 3 are of similar construction. The description below relating to one of the burners 2 applies generally to any of the other burners 2 or the burners 3.

Each burner 2 has an upwardly flared upper portion in which is provided a sintered-bronze disk 44 below a plate 43 having a plurality of upwardly open apertures. The lower tubular cylindrical stem 45 of the burner 2 is provided with a mass 46 of rolled-up metallic screening or other material for noise reduction. The lower end of the burner 2 is connected via an input mixing line 47 to a block or manifold unit 48 connected at 49 and 50 to sources of air and combustible gas. A quartz ring 53 is provided at the upper end of each of the burners 2 to prevent the entry of false air.

The burners 3 are substantially identical, having rings 54 at their upper ends and tubes 51 equivalent to the tubes 55. In addition these tubes 51 are connected via feed tubes 52 of sheet metal to respective mixing blocks 48.

Figure 1:
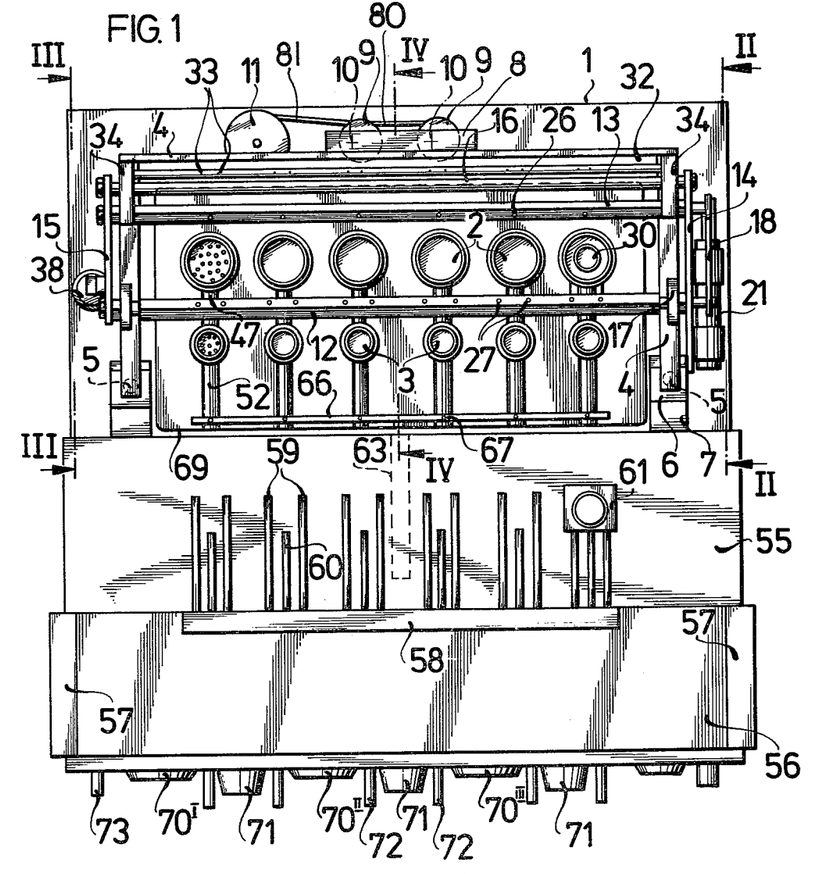
FIG. 1 is a top view of the apparatus according to this invention.

The housing 1 is provided in front of the area of the burners 2 and 3 with a horizontal cover plate 55 on which may slide a further plate 56 by means of edge guides 57. The rear edge of this plate 56 is provided with a stiffening bar 58 from which extend six pairs of holding rods 59, each pair flanking a positioning rod 60. These rods 59 and 60 are made of heatproof material, such as a ceramic, and are positioned so as to hold snugly respective mold cups 61 of platinum. In the position of FIG. 1 a cup 61 held by two such holding rods 59 and abutting a positioning rod 60 overlies the plate 55, but when slid backwardly with the plate 56 the cup 61 will lie directly over one of the warming burners 3.

Figure 4:
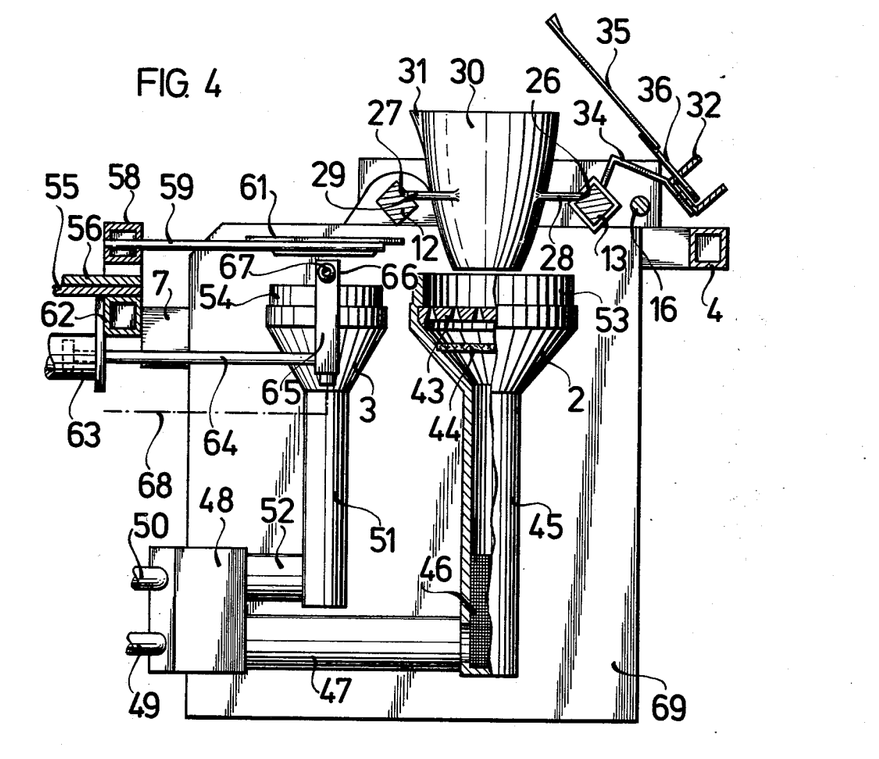

In addition, a transverse beam 62 shown in FIG. 4 is provided underneath the rear edge of the plate 55 and carries a spring-loaded pneumatic cylinder 63 of the single-acting type. This cylinder 63 has a piston rod 64 carrying on its rear end an upwardly extending hollow arm 65 in turn carrying a horizontally extending tube 66 provided on its upper surface with six equispaced holes 67. A compressed-air line 68 in which is provided a shut-off valve 73 is connected to the hollow arm 65 and thence to the interior of the tube 66.

The holes 67 are positioned so that when the cylinder 63 is pressurized fully to compress its spring each of the holes 67 lies directly over a respective one of the warming burners 3 and is therefore also upwardly directed against the lower surface of a mold cup 61 which is positioned over each of the burners 3. When the cylinder 63 is not pneumatically pressurized the tube 66 lies back almost at the rear edge of the plate 55 as shown in FIG. 1. It is noted in this context that the piston rod 64 could be connected to the slide plate 56 and the tube 66 could be permanently mounted in the position of FIG. 1 if desired.

Figure 5:
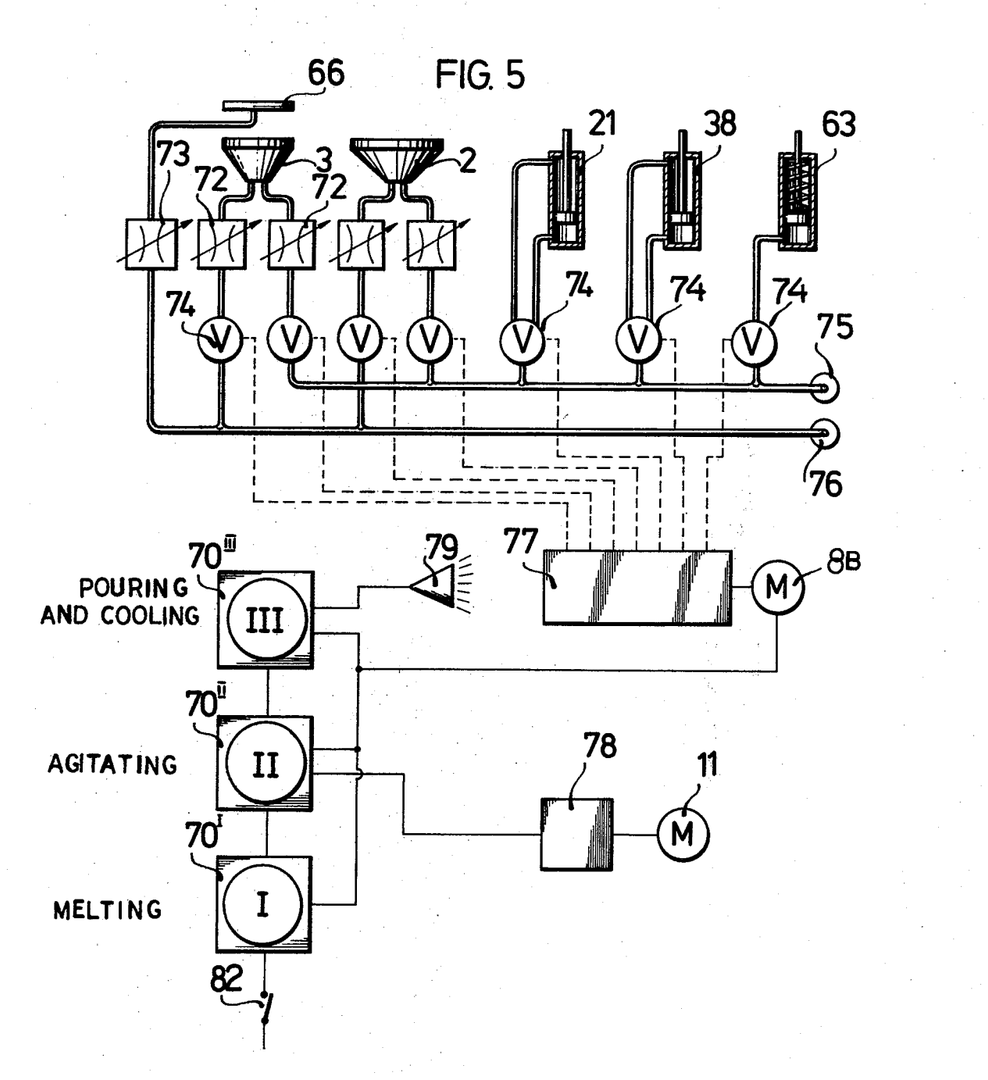
FIG. 5 is a schematic view showing the system according to this invention.

The housing 1 has a stainless-steel jacket 69 on the front of which is provided three timers $70^{I-III}$ as well as automatic ignition-control valves 71 for the various burners 2 and 3. Furthermore needle valves 72 are provided, one for the gas to each of the burners 2 or 3 and another for the air to each of the burners 2 or 3, so that a total of twelve such valves 72 is provided. In addition, as shown in FIG. 5, upstream in the fluid flow path from each of the valves 72 there is provided a cam-operable shut-off valve 74 which is connected either to a source 75 of compressed air or a source 76 of combustible gas. These valves 74 can all be operated by a three-stage cam mechanism 77 operable by means of a motor 8B by any of the timers $70^{I-III}$. One of the timers $70^{I-III}$ can also operate the motor 11 through an electronic control circuit 78 and another of the timers $70^{I-III}$ can operate an acoustical alarm 79. An on-off switch 82 is provided for operation of any of the timers $70^{I-III}$.

The system described above functions as follows:

To set the machine up the operator establishes at timer $70^{I}$ a time such as, for example, 3.5–4 minutes for melting, at timer $70^{II}$ an agitating time, and at timer $70^{III}$ a pouring and cooling time. A crucible 30 carrying the appropriate quantity of the material to be melted is placed over each of the burners 2, with its rear leg 28 engaging in a respective recess 26 and its front legs 29 in respective recesses 27. Similarly a cover 35 for each of the crucibles 30 is fitted to the holding arm 32. A mold or cup 61 is positioned on each of the holding arms 59 with the table 56 in the pulled-back position of FIG. 1. The burners 2 and 3 are then all lighted and adjusted for the proper flame. The slide 56 is then pushed backwardly to position each of the mold cups 61 over a respective one of the secondary burners 3.

The device is then started up by pushing the start button 82 so that the melting timer $70^{I}$ takes over operation of the device. During the melting phase the motor 8B controls the various valves 74 through the cam-control unit 77 so as merely to allow gas flow through the valves 72 to the burners 2 and 3 for the predetermined amount of time, normally several minutes.

Once the melting phase is over the agitating timer $70^{II}$ comes into play. Through the motor 8B the agitating timer $70^{II}$ rotates the cam selector 77 so as to pressurize the rear chamber of the cylinder 21 by means of the line 22, thereby locking the holding pins 28 and 29 between the recesses 26 and 27 and bringing each of the lids 35 snugly down over the top of each of the respective crucibles 30. Once this relatively short action is completed an electronic timer 78 operates the motor 11 so as to displace the entire frame 4 and the crucibles 30 through a small circle. The controller 78 operates the motor 11 stepwise first in one direction and then in the other for maximum mixing effect. During this agitating phase the burners 2 and 3 continue to burn, maintaining the liquid in the crucibles 30 in fused condition and heating the mold cups 61.

Finally, at the expiration of the agitating time the pouring and cooling timer $70^{III}$ takes over. Once again via the motor 83 the cam-control mechanism 77 is operated first to shut off the flow of gas and air to the burners 2 and 3 and to turn off the motor 11. Thereafter the back chamber of the cylinder 38 is pressurized via the conduit 40 to tip up the holding assembly for the crucibles 30 for a period of time of 3–4 seconds. Thus the melted and homogenized contents of these crucibles 30 are poured into the preheated mold cups 61. The preheating prevents premature quenching or chilling of the material so that a tablet of perfectly uniform consistency can be produced. Thereafter the rear chamber of the cylinder 63 is operated to displace the cooling tube 66 up above the shut-down burners 3 so that air issuing from the holes 67 cools the cups 61.

The holding assembly with the crucibles 30 is tipped back down and the front chamber of the cylinder 21 is pressurized via the line 23 to move the rods 12 and 13 into the freeing position and to lift the covers 14. The timer 70''' then actuates the alarm or acoustic warning device 79 to signal to the operator that the entire sequence is completed.

At this time the slide 56 can be pulled back and the platinum mold lifts off the arms 59. Similarly the crucibles 30 can be lifted up and replaced with freshly filled crucibles so that the operation of the device can start over again as soon as the new crucibles 30 are in place and the fresh molds 61 are also in place.

Thus with the system according to the present invention it is possible for a single operator to form tablets or disks suitable for X-ray study at a considerable production rate. This operator does not personally have to tend to the steps of melting, agitating, pouring, and cooling of the material, but need merely measure the appropriate quantities of material into the crucibles 30 and can be busy during operation of the machine with cleaning out previously used crucibles 30 and molds 61. At the beginning and end of each operation, which takes normally some eight minutes overall, the operator need merely replace the used curcibles 30 and filled molds 61 with freshly filled crucibles and new molds 61. Between the start and finish of the completely automatic operation, this operator can be busy at other tasks.

I claim:

1. An apparatus for melting and then casting a fusible material, said apparatus comprising:
   a support;
   a melting burner on said support;
   a warming burner on said support;
   a crucible having at least one holding formation;
   a crucible holder on said support having a seat for said formation and displaceable between a holding position in which said crucible is firmly held in said seat and a freeing position in which said crucible can be separated from said seat of said crucible holder;
   a mold holder on said support above said warming burner;
   a mold engageable in said mold holder, whereby said warming burner can heat said mold;
   tipping means on said support connected to said crucible holder for pivoting same between a melting position with said crucible upright above said melting burner and a pouring position with said crucible tipped and over said warming burner; and
   control means connected to said crucible holder and said tipping means for maintaining said crucible holder in said holding position at least when said seat is in said pouring position, whereby on displacement of said crucible holder from said melting into said pouring position fused material in said crucible can be poured into said mold without tipping over of said crucible.

2. The apparatus defined in claim 1 wherein a row of such melting burners and a parallel row of such warming burners are provided on said support along with a corresponding number of such crucibles, molds and mold holders, said crucible holder having a plurality of such seats each for a respective one of said crucibles.

3. The apparatus defined in claim 2 wherein said crucible holder is a pair of bars flanking said row of melting burners and each rotatable about its longitudinal axis, each bar having at each warming burner at least one radially open recess, the recesses at each warming burner constituting the seat for the respective crucible, said crucible holder further including means for pivoting said bars about their longitudinal axes between a position with said recesses pointing generally upwardly and toward each other and constituting said freeing position and a position offset generally 45° therefrom pointing generally horizontally toward each other and constituting said holding position.

4. The apparatus defined in claim 1 wherein said crucible holder is a pair of bars flanking said melting burner and each rotatable about its longitudinal axis, each bar having at said warming burner at least one radially open recess, said recesses constituting said seat for said formations.

5. The apparatus defined in claim 4 wherein said formations are pins projecting laterally from said crucible.

6. The apparatus defined in claim 5 wherein said bars are of polygonal section and each have a flat outer surface, each recess being outwardly flared and generally perpendicular to said surface.

7. The apparatus defined in claim 4 wherein said tipping means includes at least one plate in which said bars are journaled and means for tipping said plate and one of said bars about the axis of the other bar.

8. The apparatus defined in claim 7 wherein said means for tipping includes a fluid-operated cylinder operatively connected between said support and said plate.

9. The apparatus defined in claim 4, further comprising means for horizontally agitating said crucible when same is in said melting position.

10. The apparatus defined in claim 9 wherein said means for agitating includes a rotary motor carried on said support and having an output connected to said crucible holder.

11. The apparatus defined in claim 10 wherein said means for agitating further comprises a pulley centered on a pulley axis, an endless element connecting said pulley to said output, and bearing means fixed horizontally relative to said crucible holder and defining a rotation axis for said pulley offset from said pulley axis, whereby said pulley is eccentrically journaled and on rotation horizontally displaces said crucible holder.

12. The apparatus defined in claim 1 wherein said mold is a heat-resistant cup and said mold holder is displaceable between an advanced position above said warming burner and a retracted position spaced from said burner.

13. The apparatus defined in claim 12 wherein said mold holder has a pair of heat-resistant arms forming a mold seat.

14. The apparatus defined in claim 1, further comprising means for cooling said molds in said mold holder.

15. The apparatus defined in claim 14 wherein said means for cooling includes a source of gas under pressure, a conduit forming a nozzle for directing gas from siad source at siad mold, and means for displacing said holder and said conduit relatively into a juxtaposed position.

16. The apparatus defined in claim 15 wherein said means for cooling includes means for displacing said conduit into a position between said warming burner and said mold holder and said control means includes means for turning off said warming burner when siad conduit is between it and said mold holder.

17. The apparatus defined in claim 1 wherein said control means includes a plurality of valves each connected to a respective burner.

18. The apparatus defined in claim 17 wherein said control means includes a plurality of timers for sequentially operating said means of said apparatus.

19. The apparatus defined in claim 1, further comprising a lid for each crucible and means for holding said lid and for displacing same between an open position spaced from said crucible and corresponding generally to said melting position and a closed position fitting over said crucible.

20. The apparatus defined in claim 1 wherein a row of such melting burners is provided adjacent a row of such warming burners, said holder having a plurality of such seats each at a respective melting burner, said holder comprising a pair of bars flanking said row of melting burners and formed with recesses constituting said seats, said apparatus further comprising:

means for oppositely pivoting said bars from a position with said recesses of one bar directed toward said recesses of the other bar and constituting said holding position and a position with said recesses all opening generally upwardly;

means for agitating said crucible holder and crucibles held therein in a horizontal direction; and means for blowing cooling gas over said molds after same have been at least partially filled with fused material.

* * * * *